United States Patent
Napoletano et al.

(10) Patent No.: US 6,297,257 B1
(45) Date of Patent: Oct. 2, 2001

(54) BENZAZINE DERIVATIVES PHOSPHODIESTERASE 4 INHIBITORS

(75) Inventors: Mauro Napoletano, Milan; Gabriele Norcini, Varese; Daniela Botta, Como; Giancarlo Grancini; Gabriele Morazzoni, both of Milan, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/581,505

(22) PCT Filed: Dec. 17, 1998

(86) PCT No.: PCT/EP98/08292

§ 371 Date: Jul. 13, 2000

§ 102(e) Date: Jul. 13, 2000

(87) PCT Pub. No.: WO99/32449

PCT Pub. Date: Jul. 1, 1999

(30) Foreign Application Priority Data

Dec. 19, 1997 (IT) ............................... MI97A2807

(51) Int. Cl.⁷ .................................... A01N 43/42
(52) U.S. Cl. .................. 514/307; 514/309; 514/310; 546/141; 546/143; 546/144; 546/146; 546/148; 546/150
(58) Field of Search .................. 546/143, 144, 546/146, 148, 150, 141; 514/307, 310, 309

(56) References Cited

U.S. PATENT DOCUMENTS 5,556,862    9/1996  Imai et al. .................. 514/307

FOREIGN PATENT DOCUMENTS

| | | |
|---|---|---|
| 17 95 787 A | 4/1975 | (DE) . |
| 39 00 233 A | 7/1989 | (DE) . |
| 0 490 823 A | 6/1992 | (EP) . |
| WO 88 07041 A | 9/1988 | (WO) . |
| WO 97 04779 A | 2/1997 | (WO) . |
| WO 97 35854 A | 10/1997 | (WO) . |

OTHER PUBLICATIONS

J. Gardent, "Sur un aspect nouveau des dihydro–isoquinoléines Substituées en 1. Leur caractére de cétimines internes (1re partie)", Bull Soc. Chim. FR. 1957, pp. 1260–1270.

R.G. Van Inwegen et al., "Dihydro– and tetrahydroisoquinolines as inhibitors of cyclic nucleotide phosphodiesterases from dog heart—Structure–activity relationships" Biochem. Pharmacol., vol. 28, No. 8, 1979, pp. 1307–1312.

C. Lugnier et al., "Utilisation de Techniques Multiparamétriques pour Analyster la Spécifité de Différents Inhibiteurs vis–á–vis de Plusieurs Formes de Phosphodiestérases des Nuléotides Cycliques", Pharmazie, vol. 47, No. 1, 1992, pp. 46–49.

*Primary Examiner*—Bernard Dentz
(74) *Attorney, Agent, or Firm*—Arent Fox Kintner Plotkin & Kahn PLLC

(57) ABSTRACT

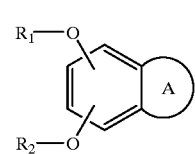

Compounds of formula (I) wherein A is an orthocondensed heterocycle optionally substituted by certain substituents and necessarily substituted by a —B—Cy group where the variables are as defined in the specification and the N→O derivatives and pharmaceutically acceptable salts thereof are phosphodiesterase-4 inhibitors.

6 Claims, No Drawings

BENZAZINE DERIVATIVES PHOSPHODIESTERASE 4 INHIBITORS

This is a 371 of International Application Serial No. PCT/EP98/08292, filed Dec. 17, 1998.

The present invention relates to benzanine derivatives, the pharmaceutical compositions comprising them and their use as phosphodiesterase 4 inhibitors.

Phosphodiesterases are a family of isoenzymes which constitutes the basis of the main mechanism of cAMP (cyclic adenosine-3',5'-monophosphate) hydrolytic inactivation. cAMP has been shown to be the second messenger mediating the biologic response to many of hormones, neurotransmitters and drugs [Krebs Endocrinology Proceedings of the 4th International Congress Excerpta Medica, 17–29, 1973]. When the suitable agonist binds the cell surface, the adenylated cyclase activates and turns $Mg^{2+}$-ATP into cAMP. cAMP modulates the activity of the majority, if not of all the cells contributing to the pathophysiology of various respiratory diseases both of allergic origin and not. It follows that an increase of cAMP concentration yields beneficial effects such as airway smooth muscle relaxation, inhibition of the mast cell mediator release (basophil granulose cells), suppression of the neutrophil and basophil degranulation, inhibition of the monocyte and macrophage activation. Thus, compounds able of activating adenylate cyclase or of inhibiting phosphodiesterases could suppress the undesired activation of the airway smooth muscle and of a great number of inflammatory cells.

In the phosphodiesterase family there is a distinct group of isoenzyines, phosphodiesterases 4 (hereinafter PDE 4) specific for the hydrolysis of the airway smooth muscle and inflammatory cells cAMP (Torphy, "Phosphodiesterase Isoenzymes: Potential Targets for Novel Anti-asthmatic Agents" in New Drugs for Asthma Barnes, ed. IBC Technical Services Ltd, 1989). Studies carried out on this enzyme show that its inhibition yields not only the airway smooth muscle relaxation, but also the mastocyte suppression, basophil and neutrophil degranulation, so as the monocyte inhibition and neutrophil activation. Furthermore the PDE 4 inhibitors activity is markedly improved when the adenylated cyclase activity of the target cells is enhanced by endogenous hormones, as the case in vivo. Thus PDE 4 inhibitors should be effective in the therapy of asthma Such compounds would offer a unique approach to the therapy of various respiratory diseases both of allergic origin and not, and possess significant therapeutic advantages over the current therapy.

The excessive or irregular production of the tumor necrosis factor (hereinafter $TNF_\alpha$), a cytokine with pro-inflammatory activity produced by various kind of cells, affects the mediation or the exacerbation of many pathologies such as, for example, the adult respiratory disease syndrome (ARDS) and the chronic pulmonary inflammatory disease. Therefore compounds able to control the negative effects of $TNF_\alpha$, i.e. the inhibitors of this cytokine, are to be considered as useful against many pathologies.

The patent application EP-0 490 823 (in the name of Sandoz) describes isoquinolines of formula

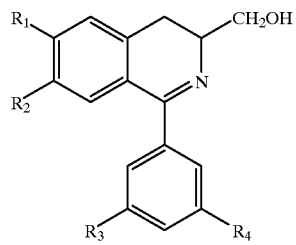

wherein $R_1$–$R_4$ are lower alkoxy groups, as PDE 3, 4 and 5 inhibitors.

The patent application EP-0 491 441 (in the name of Shell Internationale Research) claims, inter alia, isoquinoline derivatives of formula

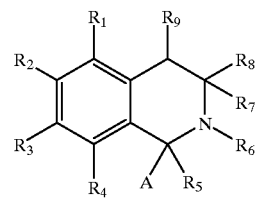

wherein $R_1$–$R_4$ are alkoxy; $R_5$ and $R_6$ are hydrogen or together form a bond; $R_7$ is hydrogen, alkyl or alkoxy; $R_8$ and $R_9$ are hydrogen or together form, a bond; and A is optionally substituted phenyl. These compounds have a fungicide activity in the agricultural field.

The patent GB 1,199,768 (in the name of Pfizer) illustrates, inter alia, compounds of formula

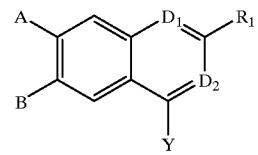

wherein A and B independently are $(C_{1-5})$alkoxy groups; $R_1$ is hydrogen or an alkyl group; $D_1$ and $D_2$ alternatively are —N= or —H=; and Y is —$NR_6R_7$ wherein $R_6$ and $R_7$ independently are hydrogen or an aryl up to 10 carbon atoms optionally substituted by 1–3 halogen atom(s). Said compounds are disclosed to be bronchodilators and antihypertensive agents.

The patent U.S. Pat. No. 5,556,862 (in the name of Nippon Zoki Pharmaceutical) claims pharmaceutical compositions containing isoquinolines of formula

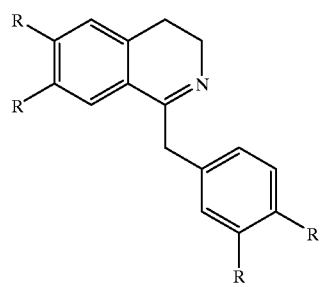

wherein Rs are hydrogen or alkoxy, useful as PDE 4 inhibitors.

The patent application WO 97/04779 (in the name of Chiroscience) claims, inter alia, quinolinones of formula

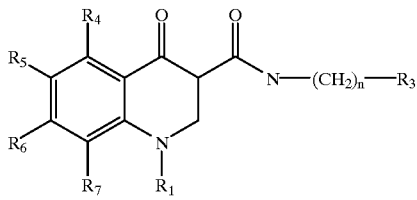

wherein $R_1$ is $(C_{1-6})$alkyl or $(C_{1-6})$alkylheterocycle optionally substituted, for example, by halogen atoms; $R_3$ is phenyl, pyridyl, furyl, etc.; $R_4$–$R_7$ are hydrogen or $(C_{1-4})$-alkoxy; and n is 0–3.

These compounds PDE 4 and $TNF_\alpha$ inhibitors.

The patent U.S. Pat. No. 5,656,643 (in the name of Rhone Poulenc Rorer) discloses compound of

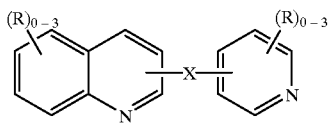

wherein X is methyl, ethyl or branched alkyl optionally interrupted by O, NH, S, SO or $SO_2$; R may be alkoxy, aralkoxy, acyloxy, halogen, alkyl, acylamino, amino, amido. These compounds are tirosin-kinase inhibitors also useful as antinflammatory drugs.

The patent application WO97/32837 (in the name of Sumitomo) claims, inter alia, compounds of formula

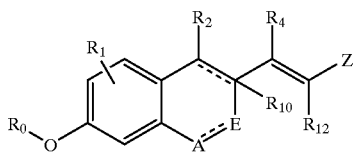

wherein $R_0$ may be a protecting group; $R_1$ may be an optionally protected hydroxy group; $R_2$ may be optionally substitued $CH_2$-aryl; $R_4$ is H or $C_{1-6}$ alkyl, A may be $CH_2$ and E may be NH or, respectively, the corresponding dehydrogenated groups when = is a double bond; $R_{10}$ and $R_{12}$ are H, $(C_{1-6})$alkyl or $(C_{1-6})$haloalkyl; Z may be COOH or $CONH_2$. These compounds are oestrogenic or anti-oestrogenic agents.

The patent application EP-0 811 613 (in the name of Pfizer) describes, inter alia, compounds of formula

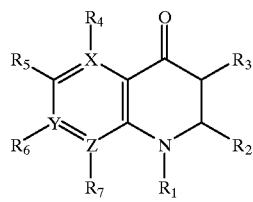

wherein $R_1$ is H, lower alkyl, phenyl optionally substituted by, for example, 1–3 halogen atom(s); $R_2$ is alkyl, alkenyl, alkynyl optionally substituted by phenyl, phenyl, naphthyl, furyl, pyridyl; $R_3$ is lower alkyl, phenyl, benzyl all being optionally substituted; $R_4$, $R_5$, $R_6$ and $R_7$ are independently H, lower alkyl, alkoxy; X, Y and Z are independently C or N. These compounds are active as antibiotics.

It has been now surprisingly found a new class of benzazine derivatives able to selectively inhibit PDE 4 and furthermore to inhibit $TNF_\alpha$.

The patent application WO97/48697 (in the name of Rhone Poulenc Rorer), published on Dec. 24, 1997, discloses, inter alia, compounds of formula

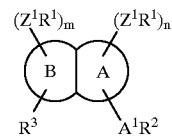

wherin A is an azaheterocycle and B an azaheteroaryl ring or an optionally halo-substituted benzene ring, $Z^1$ is a bond or an oxygen atom, $R^1$ is H or lower alkyl optionally substituted by halogen atom(s); $A^1$ is a bond or a $C_{1-6}$ alkylene optionally substituted by aryl, cycloalkyl or heteroaryl; $R^2$ may be H, aryl, heteroaryl; $R^3$ may be aryl, heteroaryl, aryl-methoxy, heteroaryl-methoxy; n and m are alternatively 0 or 1. The aryl and heteroaryl moieties may be substituted by halogen atoms. These compounds are PDE 4 and TNF inhibitors.

Therefore the present invention relates to compounds of formula I

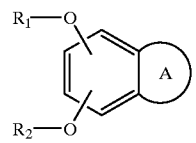

wherein A is an orthocondensed heterocycle selected from the group consisting of

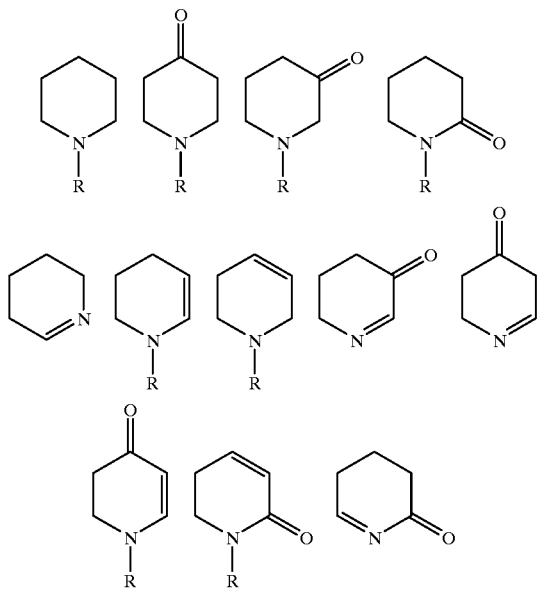

wherein R is hydrogen or a $(C_{1-4})$alkyl group, and being A optionally substituted by $(C_{1-4})$alkyl, $(C_{1-4})$alkoxy or —COOR', wherein R' is hydrogen or a $(C_{1-4})$alkyl group, and necessarily substituted by a group —B—Cy wherein B is methylene, ethylene, amino, CONH or a bond; and Cy is a 5- or 6-membered heterocycle containing from 1 to 3 nitrogen atom(s) optionally substituted by one or more halogen(s);

$R_1$ is a $(C_{1-6})$alkyl or polyfluoro$(C_{1-6})$alkyl group, $R_2$ is aryl, aryl-$(C_{1-10})$alkyl or a $(C_{4-7})$cycloalkyl optionally containing an oxygen atom and optionally substituted by a polar substituent,;

and the N→O derivatives and pharmaceutically acceptable salts thereof:

with the proviso that when R is H, $R_2$ is not arylmethyl.

The compounds of formula I may have an asymmetric centre and thus be in form of stereoisomers. Object of the present invention are compounds of formula I in form of stereoisomeric mixture so as single stercoisomers.

The compounds of formula I are active as selective PDE 4 and $TNF_\alpha$ inhibitors, and thus are used as therapeutical agents in allergic and inflammatory pathologies such as, for example, emphysema, chronic bronchitis, asthma, allergic rhinitis.

5- or 6-Membered heterocycle means pyrrole, imidazole, pyrazole, pyrrolidine, pyrroline, imidazoline, imidazolidine, pyrazolidine, pyrazoline, pyridine, pyrazine, pyrimidine, pyridazine, piperazine, piperidine, triazine, and the like, preferably pyridine and piperidine. The term halogen atom means a fluorine, chlorine, bromine or iodine atom, preferably chlorine.

Specific examples of alkyl groups are methyl, ethyl, n-propyl, i-propyl, n-butyl, s-butyl, tert.-butyl, n-pentyl, 1-methyl-butyl, 2-ethyl-propyl, 3-methyl-butyl, 3-methyl-2-butyl, n-hexyl and the like. As $(C_{4-7})$cycloalkyl group it is meant cyclobutyl, cyclopentyl, cyclohexyl and cycloheptyl, and when it contains an oxygen atom it is meant, for example, tetrahydrofuran or tetrahydropyran, while aryl and aryl-$(C_{1-10})$alkyl mean a ring or a 6–10 carbon atoms aromatic system such as, for example, phenyl, benzyl, phenethyl, phenyl-pentyl, naphthyl, indanyl, indanyl-pentyl and the like. As "polar substituent" it is meant a moiety made by atoms having different electronegativity such to create a dipole such as, for example, an hydroxy or oxo group. The N→O group optionally present in the compounds of the invention may be both on the benzazine nitrogen atoms, and on the ones present in the Cy substitutent.

Preferred compounds of the present invention are those wherein B is methylene and Cy is a 6-membered heterocycle containing from 1 to 3 nitrogen atom(s) substituted by one or more halogen(s), and the pharmaceutically acceptable salts thereof.

Still more preferred are the compounds of formula I wherein A is

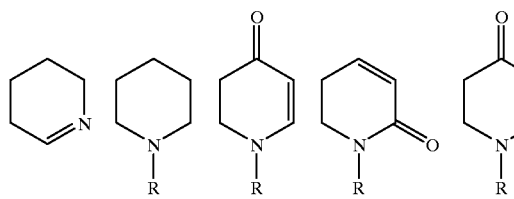

optionally substituted by $(C_{1-4})$alkyl or —COOR', wherein R' is as defined above; B is methylene and Cy is a 6-membered heterocycle containing from 1 to 3 nitrogen atom(s) substituted by one or more halogen(s), and the pharmaceutically acceptable salts thereof.

Pharmaceutically acceptable salts of the compounds of formula I are salts with organic and inorganic acids such as, for example hydrochloric, hydrobromic, hydroiodic, nitric, sulfuric, phosphoric, acetic, benzoic, maleic, fumaric, succinic, tartaric, citric, aspartic, methansulfonic and 3,7-di-tert.butylnaphthalen-1,5-disulfonic (dibudinic acid).

The preparation of the compounds of formula I proceed according to methods known to the skilled in the art of the quinolines and isoquinolines (see, for example, *Chemistry of Heterocy-clic Compounds, NY, London*). Hereinafter the synthesis of some compounds of formula I is more specifically illustrated.

When compounds of formula I having the structure of a dihydroisoquinoline are desired, the synthesis starts from a compound of formula II

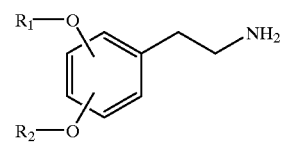

(II)

wherein $R_1$ and $R_2$ are as defined above. This is reacted with a compound of formula III

Cy—B—Y (III)

wherein Cy and B are as defined above and Y is a carboxy group or a reactive derivative thereof such as, for example, the acid chloride. When Y is a carboxy group the reaction is effected in the presence of activating agents such as, for example, 1-hydroxybenzotriazole (HOBT), dicyclohexylcarbodiimide (DCC) or carbonyldiimidazole. It is thus obtained a compound of formula IV

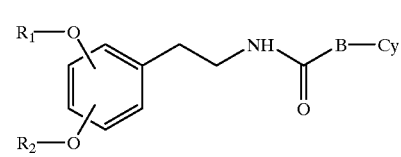

(IV)

wherein $R_1$, $R_2$, Cy and B are as defined above. This intermediate is cyclized, for example, in the presence of phosphoryl chloride, to give the desired compound of formula I.

These compounds of formula I may be reduced, for example with sodium borohydride, to give compounds of formula I wherein A is

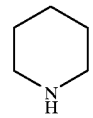

When a compound of formula I having the structure of a dihydroquinolinone or quinolinone is desired, a compound of formula V

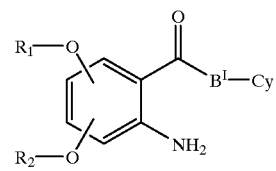

wherein $R_1$, $R_2$ and Cy are as defined above, and $B^1$ is the same as B as defined above or is $CH_2$—B, is used, which is cyclized according to methods known to the skilled in the art. For example, the compound of formula V is reacted with paraformaldehyde, thus not alkylated dihydroquinolinones of formula I are yielded, or with a suitable aldehyde, thus dihydroquinolinones of formula I substituted with ($C_{1-4}$) alkyl are obtained. Another example shows the compound of formula V to react with an aliphatic acid halide of with an anhydride, then with a base, for example, ammonia, to give quinolinones of formula I alkylated on the nitrogen ring. When ($C_{1-4}$)-alkyl substituents are not desired on the nitrogen ring, the compound of formula V is reacted with an orthoformate.

It is intended that when N-alkylated compounds of formula I are desired, the relevant alkylation reaction on the nitrogen proceeds according to method known to the skilled in the art. The synthesis of the N-oxides of the compounds of formula I is effected by treatment of the compounds of formula I with peracids such as, for example, m-chloroperbenzoic acid.

The preparation of the salts of the compounds of formula I is effected according to customary methods.

The compounds of formula I are selective PDE 4 inhibitors as shown by the inhibition tests on the isolated enzyme (example 53) without any effect on PDE 3 and 5 (example 55). Moreover they inhibit the $TNFC_\alpha$ release (example 54).

It is apparent how these receptorial selectivity and specificity features joined to the lack of activity on the cardiovascular system make the compounds of formula I particularly suitable for the treatment of the pathologies involving PDE 4 and $TNF_\alpha$, even if in the present contest the interest is particularly focused on the respiratory pathologies. Specifically the compounds of the invention are useful in the treatment of allergic and inflammatory disease and mainly in the therapy of emphysema, of the chronic pulmonary obstructive disease (COPD) and of the chronic bronchitis in particular, in asthma and allergic rhinitis.

The therapeutical doses shall be generally comprised between 0.1 and 1,000 mg a day and between 1 and 100 mg per oral route per single administration.

Furthermore object of the present invention are the pharmaceutical compositions comprising a therapeutically effective amount of the compounds of formula I or the pharmaceutically acceptable salts thereof in admixture with a suitable carrier.

The pharmaceutical compositions object of the invention may be liquid, suitable to the enteral or parenteral administration, and, preferably, solid such as tablets, capsules, granulates, suitable to the oral administration or in a form suitable for the transdermic and inhalatory administration.

The preparation of the pharmaceutical compositions object of the invention may be effected according to common techniques.

For better illustrating the present invention the following example are now provided.

EXAMPLE 1

Synthesis of 2-Cyclopentyloxy-3-methoxy-benzaldehyde

A mixture of 2-hydroxy-3-methoxy-benzaldehyde (10 g, 6.57 mmoles), $K_2CO_3$ (18.16 g, 131 mmoles), cyclopentyl-bromide (14.05 ml, 131 mmoles) in absolute ethanol (150 ml) under nitrogen was refluxed under stirring for 55 hours. The mixture was diluted with water, thrice extracted in ethyl acetate, washed with water, anhydrified over $Na_2SO_4$ and evaporated to dryness, the yielded oil was purified by flash chromatography on silica gel (eluent petrolatum/ethyl acetate 95:5) to give 8.9 g of the title product (yield: 61%).

$^1$H-NMR (200 MHz, $CDCl_3$) δ (ppm): 10.38 (s, 1H); 7.42–7.02 (m, 3H); 5.06–4.98 (s, 1H); 3.87 (s, 3H); 1.97–1.57 (m, 8H).

EXAMPLE 2

Synthesis of 2-Cyclopentyloxy-1-methoxy-3-(2-nitro-vinyl)-benzene

A solution of 2-cyclopentyloxy-3-methoxy-benzaldehyde (8.8 g, 39.95 mmoles), obtained as described in example 1, in methanol (50 ml) was sequentially added under stirring with 8.03M methylamine (1.05 ml, 8.43 mmoles) in ethanol, acetic acid (0.482 ml, 8.43 mmoles) and nitromethane (2.36 ml, 43.94 mmoles). The mixture was heated to 40° C. for 9 hours, then left overnight at room temperature. The product precipitated in crystalline form was filtered and dried under vacuum at 40° C. to give 8.14 g of the title product (yield: 77%).

$^1$H-NMR (200 MHz, $CDCl_3$) δ (ppm): 8.26 (d, 1H, JHH=13.8 Hz); 7.65 (d, 1H); 7.97–6.96 (m, 3H); 5.044.97 (m, 1H); 3.86 (s, 3H); 1.90–1.57 (m, 8H).

EXAMPLE 3

Synthesis of 2-(2-Cyclopentyloxy-3-methoxy-phenyl)-ethylamine Hydrochloride

A slurry under nitrogen of lithium aluminium hydride (3.5 g, 92.28 mmoles) in dry tetrahydrofuran (35 ml) was dropwise added under stirring with a solution of 2-cyclopentyloxy-1-methoxy-3-(2-nitro-vinyl)-benzene (8.1 g, 30.76 mmoles), obtained as described in example 2, in dry tetrahydrofuran (100 ml). At the end of the addition the mixture was refluxed for 2 hours more, then cooled in ice and slowly added with water (3.5 ml), 15% NaOH (3.5 ml) and water again (10.5 ml). Off the cooling bath, the stirring was kept on for another hour, then the solid was filtered off, and the solution was concentrated to small volume, diluted with ethyl acetate, washed with water, anhydrified over $Na_2SO_4$ and dried to give an oil which was dissolved in ethyl acetate (100 ml) and acidified with HCl/ethyl acetate. The product crystallized, thus was filtered and dried under vacuum at 40° C. to give 6.07 g of the title product (yield: 73%).

$^1$H-NMR (200 MHz, DMSO) δ (ppm): 7.89 (m, 3H); 7.01–6.75 (m, 3H); 4.86–4.79 (m, 1H); 3.76 (s, 3H); 2.95–2.77 (m, 4H); 1.90–1.57 (m, 8H).

EXAMPLE 4

Synthesis of N-[2-(2-Cyclopentyloxy-3-methoxy-phenyl)ethyl]-2-(3,5-dichloro-pyridin-4-yl)-acetamide A solution of 3,5-dichloro-pyridin-4-yl-acetic acid chloride (0.7 g, 2,68 mmoles) and 2-(2-cyclopentyloxy-3-methoxy-phenyl)-ethylamine hydrochloride (660 mg, 2.43 mmoles), obtained as described in example 3, in methylene chloride (20 ml) was added under stirring with ice-cooling, with triethylamine (1.53 ml, 9.72 mmoles). The ice-bath was removed and after 1 hour the mixture was diluted with methylene chloride, washed with water, anhydrified over $Na_2SO_4$ and dried. The residue was purified by silica gel flash chromatography (eluent: petrolatum/ethyl acetate 7:3). The solid was taken up in petrolatum, filtered and dried under vacuum at 40° C. to give 420 mg of the title product (yield: 41%).

$^1$H-NMR (200 MHz, $CDCl_3$) δ (ppm): 8.44 (s, 2H); 6.97–6.65 (m, 3H); 6.02 (t broad, 1H), 4.89–4.81 (m, 1H);

3.86 (s, 3H); 3.79 (s, 2H); 3.49–3.40 (m, 2H); 2.81–2.75 (m, 2H); 1.83–1.53 (m, 8H).

EXAMPLE 5

Synthesis of 5-Cyclopentyloxy-1-(3,5-dichloro-2-pridin-4-yl-methyl)-6-methoxy-3,4-dihydro-isoquinoline Hydrochloride (Compound 1)

A solution under nitrogen of N-[2-(2-cyclopentyloxy-3-methoxy-phenyl)ethyl]-2-(3,5-dichloro-pyridin-4-yl)-acetamide (400 mg, 0.945 mmoles), obtained as described in example 4, in acetonitrile (10 ml) and phosphoryl chloride (0.182 ml, 1.984 mmoles) was refluxed under stirring for 3 hours, then evaporated to dryness, dissolved in methylene chloride, thrice washed with a solution of $NaHCO_3$, and with water, anhydrified over $Na_2SO_4$ and concentrated to small volume, the concentrate was acidified with HCl/ethyl acetate and dried. The residue was taken up in ethyl acetate and filtered to give, after drying under vacuum et 40° C., 350 mg of the title product (yield: 50%).

$^1$H-NMR (200 MHz, $CDCl_3$) δ (ppm): 12.72 (m, 1H); 8.72 (s, 2H); 7.83 and 7.22 (2d, 2H, JHH=8.8 Hz); 4.91 (s broad, 2H); 4.86–4.77 (m, 1H); 3.94 (s, 3H); 3.70 (t broad, 2H); 3.00 (t broad, 2H); 1.81–1.57 (m, 8H).

EXAMPLE 6

Synthesis of 4-Cyclopentyloxy-3-methoxy-benzaldehyde

A mixture of vanillin (10 g, 65.7 mmoles), cyclopentyl bromide (21.09 g, 196.7 mmoles), tetrabutylammonium bromide (211.8 mg, 0.675 mmoles) and $K_2CO_3$ (27.16 g, 199.48 mmoles) in tetrahydrofuran/water 8:2 (200 ml) was refluxed under nitrogen and vigorous stirring for 55 hours, then diluted with water, extracted with ethyl acetate, and the extract was washed with water, anhydrified over $Na_2SO_4$ and dried to give an oil which was purified by silica gel flash chromatography (eluent: petrolatum/ethyl acetate 9:1) and gave 14 g of the title product (yield: 97%).

$^1$H-NMR (200 MHz, $CDCl_3$) δ (ppm): 9.81 (s, 1H); 7.42–6.91 (m, 3H); 4.89–4.80 (m, 1H); 3.88 (s, 3H); 2.08–1.53 (m, 8H).

EXAMPLE 7

Synthesis of 1-Cyclopentyloxy-2-methoxy-4-(2-nitro-vinyl)-benzene

A solution of 4-cyclopentyloxy-3-methoxy-benzaldehyde (13.95 g, 63.33 mmoles), obtained as described in example 6, in methanol (7 ml) was sequentially added under stirring, with 8.03M methylamine in ethanol (1.66 ml, 13.36 mmoles), acetic acid (0.76 ml, 13.36 mmoles) and nitromethane (3.74 ml, 69.66 mmoles), then the mixture was heated to 40° C. under stirring for 1 night, dried and the residue was purified by silica gel flash chromatography (eluent: methylene chloride). The eluate was crystallized from ethyl ether+petrolatum (30 ml+60 ml) and, after drying under vacuum at 40° C., gave 7.1 g of the title product (yield: 43%).

$^1$H-NMR (200 MHz, $CDCl_3$) δ (ppm): 7.94 (d, 1H, JHH=13.6 Hz); 7.50 (d, 1H); 7.14–6.85 (m, 3H); 4.86–4.77 (m, 1H); 3.86 (s, 3H); 2.06–1.52 (m, 8H).

EXAMPLE 8

Synthesis of 2-(4-Cyclopentyloxy-3-methoxy-phenyl)ethylamine Hydrochloride

A slurry under nitrogen of lithium aluminium hydride (3.05 g, 80.34 mmoles) in dry tetrahydrofuran (30 ml), was dropwise added under stirring with a solution of 1-cyclopentyloxy-2-methoxy-4-(2-nitro-vinyl)-benzene (7.05 g, 26.78 mmoles), obtained as described in example 7, in dry tetrahydrofuran (100 ml). At the end of the addition the mixture was refluxed for 2 hours, then cooled in ice and slowly added with water (3.05 ml), 15% NaOH (3.05 ml) and water again (9.15 ml). Off the cooling bath, the stiring was kept on for another hour, then the solid was filtered off and the solution was concentrated to small volume, diluted with ethyl acetate, washed with water, anhydrified over $Na_2SO_4$ and dried to give an oil which was dissolved in ethyl acetate (100 ml) and acidified with HCl/ethyl acetate. The product crystallized, thus was filtered and dried under vacuum at 50° C. to give 5.14 g of the title product (yield: 71%).

$^1$H-NMR (200 MHz, DMSO) δ (ppm): 8.08 (m, 3H); 6.87–6.68 (m, 3H); 4.75–4.67 (m, 1H); 3.73 (s, 3H); 3.02–2.75 (m, 4H); 1.88–1.49 (m, 8H).

EXAMPLE 9

Synthesis of N-[2-(4-Cyclopentyloxy-3-methoxy-phenyl)-ethyl]-2-(3,5-dichloro-pyridin-4-yl)-acetamide A solution of (3,5-dichloro-pyridin-4-yl)-acetic acid chloride (680 mg, 2.61 mmoles) and 2-(4-cyclopentyloxy-3-methoxy-phenyl)-ethylamine hydrochloride (645 mg, 2.37 mmoles), obtained as described in example 8, in methylene chloride (20 ml) was added under stirring in ice-cooling with triethylamine (1.32 ml, 9.48 mmoles). The ice-bath was removed and after 1 hour the mixture was diluted with methylene chloride, washed with water, anhydrified over $Na_2SO_4$ and dried. The residue was purified by silica gel chromatography (eluent: petrolatum/ethyl acetate 1:1). The solid was taken up in petrolatum, filtered, dried under vacuum at 40° C. to give 350 mg of the title product (yield 35%)

$^1$H-NMR (200 MHz, $CDCl_3$) δ (ppm): 8.46 (s, 2H); 6.76–6.65 (m, 3H); 5.43 (t broad, 1H); 4.76–4.67 (m, 1H), 3.83 (s, 2H); 3.80 (s, 3H); 3.53–3.44 (m, 2H); 2.75–2.68 (m, 2H); 1.98–1.51 (m, 8H).

EXAMPLE 10

Synthesis of 7-Cyclopentyloxy-1-(3,5-dichloro-pyridin-4-yl-methyl)-6-methoxy-3,4-dihydro-isoquinoline Hydrochloride (Compound 2)

A solution of N-[2-(4-cyclopentyloxy-3-methoxy-phenyl)ethyl]-2-(3,5-dichloro-pyridin-4-yl)-acetamide (330 mg, 0.78 mmoles), obtained as described in example 9, in acetonitrile (10 ml) and phosphoryl chloride (0.15 ml, 1.683 mmoles) was refluxed under nitrogen and stirring for 2 hours, then dried, dissolved in methylene chloride, thrice washed with a solution of $NaHCO_3$, and with water, anhydrified over $Na_2SO_4$ and concentrated to small volume. The concentrate was acidified with HCl/ethyl acetate and dried. The residue was taken up methyl acetate and filtered to give, after drying under vacuum at 40° C., 310 mg of the title product (yield: 90%).

$^1$H-NMR (200 MHz, $CDCl_3$) δ (ppm): 13.04 (m, 1H); 8.71 (s, 2H); 7.20 and 7.19 (2s, 2H); 4.96 (s broad, 2H); 4.74–4.67 (m, 1H); 3.89 (s, 3H); 3.80–3.72 (m, 2H); 1.86–1.50 (m, 8H).

EXAMPLE 11

Synthesis of Methansulfonic Acid 5-phenyl-pentyl Ester

5-Phenyl-pentanol (40 g, 244 mmoles) in methylene chloride (80 ml) at 0° C. was added with triethylamine (39 ml, 28.34 g, 280 mmoles) and a solution of methyl-sulfonyl chloride (20.7 ml, 30.69 g, 268 mmoles) in methylene chloride (40 ml). The temperature was left to rise to the room value, then the mixture was poured into water and the organic phase was isolated, washed with water, anhydrified and concentrated to give 59.49 g of the title product (yield: 99%).

$^1$H-NMR (200 MHz, CDCl$_3$) δ (ppm): 7.31–7.13 (m, 5H); 4.20 (t, 2H, JHH=6.5 Hz); 2.96 (s, 3H); 2.65–2.57 (m, 2H); 1.83–1.34 (m, 6H).

EXAMPLE 12

Synthesis Di 2-(5-Penylpentiloxy)-3-methoxy-benzaldehyde

Operating analogously to example 1 using 2-hydroxy-3-methoxy-benzaldehyde (12.49 g, 82.1 mmoles), methansulfonic acid 5-phenyl-pentyl ester (29.84 g, 147.5 mmoles), obtained as described in example 11, Na$_2$CO$_3$ (17.4 g, 164 mmoles), KI in catalytic amount and dimethylfomiamide (130 ml), 24.37 g of the title product were obtained (quantitative yield).

$^1$H-NMR (200 MHz, CDCl$_3$) δ (ppm): 10.43 (s, 1H); 7.43–7.09 (m, 8H); 4.1 (t, 2H, JHH=6.7 Hz); 3.86 (s, 3H); 2.67–2.60 (m, 2H); 1.90–1.43 (m, 6H).

EXAMPLE 13

Synthesis of 2-(5-Phenylpentyloxy)-1-methoxy-3-(2-nitro-vinyl)-benzene

Operating analogously to example 2 using 2-(5-phenylpentyloxy)-3-methoxy-benzaldehyde (1 g, 3.35 mmoles), obtained as described in example 12, 8.03M methylamine in ethanol (0.088 ml, 0.7035 mmoles), acetic acid (0.04 ml, 0.7035 mmoles) and nitromethane (0.198 ml, 3.685 mmoles) in methanol (5 ml), 0.56 g of the title product was obtained (yield: 49%).

$^1$H-NMR (200 MHz, CDCl$_3$) δ (ppm): 8.24 (d, 1H, JHH=13.7 Hz); 7.72 (d, 1H); 7.31–6.98 (m, 8H); 4.04 (t, 2H, JHH=6.5 Hz); 3.85 (s, 3H); 2.68–2.61 (m, 2H, JHH=6.8 Hz); 1.90–1.44 (m, 1H).

EXAMPLE 14

Synthesis of 2-[2-(5-Phenylpentyloxy)-3-methoxy-phenyl]-3-ethylamine

Operating analogously to example 3 using lithium aluminium hydride (5.83 g, 154 mmoles), 2-(5-phenylpentyloxy)-1-methoxy-3-(2-nitro-vinyl)-benzene (17.48 g, 51.20 mmoles), obtained as described in example 12, in dry tetrahydrofuran (270 ml), without salifying the base, 15.53 g of the title product were obtained (yield: 97%).

$^1$H-NMR (200 MHz, CDCl$_3$) δ (ppm): 7.31–6.73 (m, 8H); 3.91 (t, 2H, JHH=6.5 Hz); 3.81 (s, 3H); 2.94–2.60 (m, 6H); 1.87–1.32 (m, 8H).

EXAMPLE 15

Synthesis of 3,5-Dichloro-4-methyl-pyiridine

A solution under nitrogen of diisopropylamine (53.43 ml, 0.25 moles) in dry tetrahydrofuran (350 ml) was added, under stirring at −20° C., with 2.5M n-butyl-lithium in hexane (100 ml, 0.25 moles), and the mixture was stirred for 30 minutes at fixed temperature, then cooled to −78° C. and added with a solution of 3,5-dichloro-pyridine (35.2 g, 0.238 moles) in dry tetrahydrofuran (200 ml). At the end of the addition the stirring was kept on for 40 minutes at fixed temperature then methyl iodide (15.56 ml, 0.25 moles) was added and the stirring was kept on for 15 minutes at fixed temperature. After 1 night at room temperature, the mixture was added with a concentrated solution of NH$_4$Cl, concentrated to small volume, diluted with water, thrice extracted in ethyl acetate, and the extract was thrice washed with water, anhydrified over Na$_2$SO$_4$, discoulored with charcoal and dried. The residue was crystallized from ethanol (100 ml) by adding water (100 ml) under stirring with cooling. After filtering and drying under vacuum over P$_2$O$_5$, 26 g of the title product were obtained (yield: 67%).

$^1$H-NMR (200 MHz, CDCl$_3$) δ (ppm): 8.38 (s, 2H); 2.45 (s, 3H).

EXAMPLE 16

Synthesis of 2-(3,5-Dichloro-pyridin-4-yl)acetic Acid Methyl Ester 3,5-dichloro-4-methyl-pyridine (25 g, 0.15 moles), obtained as described in example 15, was dissolved in dimethylformamide (100 nl) under nitrogen and added with 55% NaH (7.4 g, 0.17 moles), then with methoxy-methyl carbonate (42.8 ml, 0.51 moles). The mixture was stirred for 1 night, then poured into pH=7 buffer and extracted in pentane. The organic phase was dried and the residue purified by silica gel flash chromatography (eluent: petrolatum 100%., then petrolatum/ethyl ether 95:5 and 9:1) to give 24.2 g of the title product (yield: 73%).

$^1$H-NMR (200 MHz, CDCl$_3$) δ (ppm): 8.48 (s, 2H); 3.98 (s, 2H); 3.71 (s, 3H).

EXAMPLE 17

Synthesis of 2-(3,5-Dichloro-pyridin-4-yl)acetic Acid 2-(3,5-dichloro-pyridin-4-yl)acetic acid methyl ester (24.2 g, 0.11 moles), obtained as described in example 16, was dissolved in methanol (165 ml) and added with 1N NaOH (165 ml). After 40 minutes 1N HCl was added (165 ml) and the formed precipitate was filtered to give 18.75 g of the title product (yield: 91%).

$^1$H-NMR (200 MHz, CDCl$_3$) δ (ppm): 8.50 (s, 2H); 7.60 (m, 1H); 4.02 (s, 2H).

EXAMPLE 18

Synthesis of N-{2-[2-(5-phenylpentyloxy)-3-methoxy-phenyl]ethyl}-2-(3,5-dichloro-pyridin-4-yl)-acetamide 2-(3,5-dichloro-pyridin-4-yl)acetic acid (5.78 g, 28.1 mmoles) obtained as described in example 17, was dissolved in tetrahydrofuran, added with 1-hydroxy-benzotriazole (3.79 g, 2.1 mmoles) then DCC (5.73 g, 28.1 mmoles). After 1 hour under stirring 2-[2-(5-phenylpentyloxy)-3-methoxy-phenyl]-ethylamine (8 g, 25.5 mmoles), obtained as described in example 14 was added and the stirring kept on for 2 hours more. The resulting solid was filtered and dried, taken up in ethyl acetate. The new solid was filtered off and the mother liquor dried to give a residue which was dissolved in NaHCO$_3$ and ethyl acetate. The organic phase was washed with water and dried. The residue was purified by silica gel flash chromatography (eluent: petrolatum/ethyl acetate 8:2 then 7:3) to give 9.01 g of the title product (yield:70%).

$^1$H-NMR (200 MHz, CDCl$_3$) δ (ppm): 8.43 (s, 2H); 7.30–6.64 (m, 8H); 5.97 (t broad, 1H); 3.86 (t, 2H, JHH=6.5 Hz); 3.83 (s, 3H); 3.77 (s, 2H); 3.49–3.4 (m, 2H); 2.79–2.72 (m, 2H); 2.66–2.59 (m, 2H); 1.78–1.36 (m, 6H).

EXAMPLE 19

Synthesis of 1-(3,5-Dichloro-pyridin-4-yl-methyl)-5-(5-phenylpentyloxy)-6-methoxy-3,4-dihydro-isoquinoline Hydrochloride (Compound 3)

A solution of N-{-2-[2-(5-phenylpentyloxy)-3-methoxy-phenyl]ethyl}-2-(3,5-dichloro-pyridin-4-yl)-acetamide (7.8 g, 15.55 mmoles), obtained as described in example 18, and phosphoryl chloride (22.24 ml, 243.4 mmoles) in toluene (150 ml) was heated to 80° C. for 1 night, then cooled, diluted with toluene and added with NaHCO$_3$ till alkalinity. The organic phase was washed with water till neutrality, anhydrified and concentrated to give an oil which was chromatographed (flash) on silica gel (eluent: petrolatum/ethyl acetate 7:3) to give 2.48 g of base and a mixture base+reagent. A quota of this mixture was dissolved in ethyl ether, acidified with etheric HCl, and the precipitate was filtered, washed with ethyl ether and dried to give 1.18 g of the title product (yield: 97.8%).

$^1$H-NMR (200 MHz, DMSO-d6) δ (ppm): 13.20 (m, 1H); 8.69 (s, 2H); 7.77 (d, 1H, JHH=9 Hz); 7.3–7.11 (m, 6H); 4.95 (s broad, 2H); 3.94–3.88 (m, 2H); 3.91 (s, 3H); 2H); 3.04–2.96 (m, 2H); 2.62–2.55 (m, 2H); 1.76–1.34 (m, 6H).

EXAMPLE 20

Synthesis of 1-(3,5-dichloro-pyridin-4-yl-methyl)-5-(5-phenylpentyloxy)-6-methoxy-1,2,3,4-tetrahydro-isoquinoline Dihydrochloride (Compound 4)

A solution of 1-(3,5-dichloro-pyridin-4-yl-methyl)-5-(5-phenylpentyloxy)-6-methoxy-3,4-dihydroisoquinoline (0.31 g, 9.64 mmoles), obtained as described in example 19, in methanol (10 ml) and dioxane (2 ml) was added with NaBH$_4$ (0.48 g, 12.8 mmoles). After 1 hour the reaction mixture was dried to give a residue which was purified by silica gel flash chromatography (eluent: petrolatum/ethyl acetate 7:3) thus yielding 0.174 g of base which was dissolved in ethyl ether and few of methylene chloride, then acidified with etheric HCl. The resulting precipitate was filtered and dried in oven to give 0.17 g of the title product (yield: 48%).

$^1$H-NMR (200 MHz, DMSO-d6) δ (ppm): 9.75 (m, 2H); 8.62 (s, 2H); 7.31–7.12 (d, 1H, JHH=8.7 Hz); 6.36 (d, 1H); 4.78–4.63 (m, 1H); 3.93–3.83 (m, 2H); 3.73 (s, 3H); 3.54 (d, 2H, JHH=7.4 Hz); 3.62–2.83 (m, 4H); 2.63–2.56 (m, 2H); 1.76–1.35 (m, 6H).

EXAMPLE 21

Synthesis of 4-(5-Phenylpentyloxy)-3-methoxy-benzaldehyde

A solution of vanillin (12.49 g, 82.1 mmoles) in dimethylformamide was added with Na$_2$CO$_3$ (17.4 g, 164 mmoles) and KI (catalytic amount). The mixture was brought to 90° C. then slowly added with methansulfonic acid 5-phenyl-pentyl ester (24.87 g, 103 mmoles) obtained as described in example 11, in dimethylformamide (40 ml). After 1.5 hours the mixture was poured into 1N HCl and thrice extracted with pentane, anhydrified and dried. The residue was purified by silica gel flash chromatography (eluent: petrolatum/ethyl acetate 9:1), so 7.46 g of the title product were obtained (yield: 97%).

$^1$H-NMR (200 MHz, CDCl$_3$) δ (ppm): 9.83 (s, 1H); 7.43–6.91 (m, 8H); 4.08 (t, 2H, JHH=6.6 Hz); 3.90 (s, 3H); 2.67–2.59 (m, 2H); 1.94–1.42 (m, 6H).

EXAMPLE 22

Synthesis of 1-(5-Phenylpentyloxy)-2-methoxy-4-(2-nitro-vinyl)-benzene

Operating analogously to example 2 using 4-(5-phenylpentyloxy)-3-methoxy-benzaldehyde (21 g, 73.4 mmoles), obtained as described in example 21, in methanol (86 ml), 8.03M methylamine in ethanol (1.92 ml, 15.4 mmoles), acetic acid (0.88 ml, 15.4 mmoles) and nitromethane (4.34 ml, 80.7 mmoles) 20 g of the title product were obtained (yield: 80%).

$^1$H-NMR (200 MHz, CDCl$_3$) δ (ppm): 7.94 (d, 1H, JHH=13.5 Hz); 7.50 (d, 1H); 7.30–6.83 (m, 8H); 4.05 (t, 2H, JHH=6.7 Hz); 3.88 (s, 3H); 2.67–2.59 (m, 2H, JHH=6.8 Hz); 1.94–1.42 (m, 6H).

EXAMPLE 23

Synthesis of 2-[4-(5-Phenylnentyloxy)-3-methoxy-phenyl]-ethylamine

Operating analogously to example 3 using lithium aluminium hydride (9 g, 237.3 mmoles) in dry tetrahydrofuran (89 ml) and 1-(5-phenylpentoxy)-2-methoxy-3-(2-nitro-vinyl)-benzene (20 g, 58.58 mmoles), obtained as described in example 22, in dry tetrahydrofuran (390 ml), 17.89 g of the title product were obtained (yield: 97%).

$^1$H-NMR (200 MHz, CDCl$_3$) δ (ppm): 7.30–6.66 (m, 8H); 3.97 (t, 2H, JHH=6.8 Hz); 3.83 (s, 3H); 2.93 (t, 2H, JHH=6.8 Hz); 2.70–2.58 (m, 4H); 1.92–1.40 (m, 8H).

EXAMPLE 24

Synthesis of N-{2-[4-(5-Phenylpentyloxy)-3-methoxy-phenyl]ethyl}-2-(3,5-dichloro-pyridin-4-yl)-acetamide 2-(3,5-Dichloro-pyridin-4-yl)acetic acid (6.78 g, 28 mmoles), obtained as described in example 17, was dissolved in tetrahydrofuran (100 ml), was added with HOBT (3.79 g, 28 mmoles) then with DCC (5.79 g, 28 mmoles). After 30 minutes under stirring 2-[2-(5-phenylpentyloxy)-3-methoxy-phenyl]-ethylamine (8 g, 25.5 mmoles), obtained as described in example 23, was added and the stirring was kept on for 1 night. The resulting solid was filtered and taken up in ethyl acetate. The new solid was filtered off and the dried mother liquor gave a residue which was dissolved in NaHCO$_3$ and ethyl acetate. The organic phase was washed with water and dried. The residue was purified by silica gel flash chromatography (eluent: petrolatum/ethyl acetate 6:4) to give 2.89 g of the title product (yield: 57%).

$^1$H-NMR (200 MHz, CDCl$_3$) δ (ppm): 8.45 (s, 2H); 7.29–6.57 (m, 8H); 5.42 (t broad, 1H); 3.97 (t, 2H, JHH=6.7 Hz); 3.83 (s, 2H); 3.81 (s, 3H); 3.54–3.44 (m, 2H); 2.76–2.59 (m, 2H); 1.93–1.41 (m, 6H).

EXAMPLE 25

Synthesis of 1-(3,5-Dichloro-pyridin-4-yl-methyl)-7-(5-phenylpentyloxy)-6-methoxy-3,4-dihyidro-isoquinoline hydrochloride (Compound 5)

Operating analogously to example 19 using N-{2-[4-(5-phenylpentyloxy)-3-methoxy-phenyl]-ethyl}-2-(3, 5dichloro-pyridin-4-yl)-acetamide (6.89 g, 13.7 mmoles), obtained as described in 30 example 24, and phosphoryl chloride (12.58 ml, 137 mmoles) in toluene (170 ml) 2.145 g of the title product were obtained (yield: 28.1%).

$^1$H-NMR (200 MHz, DMSO-d6) δ (ppm): 13.40 (m, 1H); 8.65 (s, 2H); 7.27–7.10 (m, 7H); 4.98 (s, 2H); 3.88 (s, 3H); 3.91–3.84 (m, 2H); 3.78–3.70 (m, 2H); 3.06–2.98 (m, 2H); 2.60–2.48 (m, 2H); 1.74–1.29 (m, 6H).

EXAMPLE 26

Synthesis of 1-(3,5-Dichloro-pyridin-4-yl-methyl)-7-(5-phenylpentyloxy)-6-methoxy-1,2,3,4-tetrahydro-isoquinoline Hydrochloride (Compound 6)

Operating analogously to example 20 using 1-(3,5-dichloro-pyridin-4-yl-methyl)-7-(5-phenyl-pentyloxy)-6-methoxy-3,4-dihydro-isoquinoline (0.3 g, 6.62 mmoles), obtained as described in example 25, in methanol and dioxane (10+2 ml) and NaBH$_4$ (0.47 g, 12.4 mmoles) 0.148 g of the title product was obtained (yield: 41%).

$^1$H-NMR (200 MHz, DMSO-d6) δ (ppm): 9.76 (m, 2H); 8.60 (s, 2H); 7.31–7.12 (m, 5H); 6.81 and 5.90 (2s, 2H); 4.66–4.59 (m, 1H); 3.64–3.00 (m, 8H); 3.71 (s, 3H); 2.61–2.53 (m, 2H); 1.65–1.27 (m, 6H).

EXAMPLE 27

Synthesis of 3-Hydroxy-4-methoxy-2-nitro-benzaldehyde and 3-Hydroxy-4-methoxy-6-nitro-benzaldehyde In a suspension of isovanillin (50 g, 0.33 moles) in acetone (250 ml), under nitrogen at 0–5° C., 70% nitric acid (25 ml, 0.4 moles) was dropped and the mixture was kept under cooling till total dissolution, then at 20° C. for 2.5 hours. The mixture was poured into water (3 l) and ice (1 kg) under stirring for 30 minutes, and the formed precipitate was filtered, washed with water and dried at 60° C. over P$_2$O$_5$ for 1 night to give 47.9 g of a 6:4 mixture of the two title products (yield: 74%).

Ortho product: $^1$H-NMR (200 MHz, DMSO-6) δ (ppm): 9.72 (s, 1H); 7.45 (d, 1H, JHH=8.3 Hz); 7.26 (d, 1H); 3.94 (s, 3H).

Para product: $^1$H-NMR (200 MHz, DMSO-d6) δ (ppm): 11.04 (m, 1H); 10.16 (sm, 1H); 7.68 and 7.2 (2s, 2H); 3.94 (s, 3H).

EXAMPLE 28

Synthesis of 3-Cyclopentyloxy-4-methoxy-2-nitro-benzaldehyde and 3-Cyclopentyloxy-4-methoxy- 6-nitro-benzaldehyde A mixture under nitrogen of 3-hydroxy-4-methoxy-2-nitro-benzaldehyde and 3-hydroxy-4-methoxy-6-nitro-benzaldehyde (2.9 g, 15 moles), obtained as described in example 27, in dimethylformamide (30 ml) was added with Na$_2$CO$_3$ (3.2 g, 30 moles) and the suspension was heated to 80° C. Cyclopentyl bromide (2.76 ml, 25.5 moles) in dimethylformamide (2.5 ml) was dropped therein then the mixture was left at 80° C. overnight under stirring, then cooled, poured into water (400 ml) and thrice extracted in ethyl acetate. The organic extracts were washed with an aqueous solution of NaCl, discoloured with charcoal, anhydrified and dried under vacuum. The residue was purified by silica gel flash chromatography (eluent: petrolatum 40:60°/ ethyl ether 6:4) to give 1.08 g of the two title products (total yield: 66%).

Ortho product: $^1$H-NMR (200 MHz, CDCl$_3$) δ (ppm): 9.76 (s, 1H); 7.58 (d, 1H, JHH=8.6 Hz); 7.06 (d, 1H); 3.97 (s, 3H); 1.88–1.49 (m, 8H).

Para product: $^1$H-NMR (200 MHz, CDCl$_3$) δ (ppm): 10.42 (s, 1H); 7.57 and 7.36 (2s, 2H); 4.97–4.87 (m, 1H); 3.97 (s, 3H); 2.11–1.55 (m, 8H).

EXAMPLE 29

Synthesis of 1-(3-Cyclopentyloxy-4-methoxy-2-nitro-phenyl)-2-(3,5-dichloro-pyridin-4-yl-methyl)-ethanol A 2M solution under nitrogen of lithium diisopropylamide in tetrahydrofuran/heptane/ethylbenzene (47 ml, 94.9 mmoles) in dry tetrahydrofuran (100 ml) was added with 3,5-dichloro-4-methyl-pyridine (14.6 g, 90.4 mmoles), obtained as described in example 15, in dry tetrahydrofuran (100 ml), keeping the temperature under –65° C. At the end of the addition the mixture was left under stirring for 1 hour at –75° C., then added with 3-cyciopentyloxy-4-methoxy-2-nitro-benzaldehyde (24 g, 90.4 mmoles), obtained as described in example 28, in dry tetrahydrofuran (100 ml), keeping the temperature under –68° C. At the end of the addition the mixture was left under stirring for 1.5 hours at –72° C., then treated with NH$_4$Cl (200 ml), heated to room temperature, diluted with water. The aqueous phase was twice extracted in ethyl acetate. The organic phases were discoloured with charcoal, anhydrified and dried under vacuum. The residue was tritured with isopropyl ether to give 4.76 g of the title product (yield: 84%).

$^1$H-NMR (200 MHz, CDCl$_3$) δ (ppm): 8.96 (s, 2H); 7.26–7.00 (2s, 2H, JHH=8.8 Hz); 5.10–4.99 (m, 2H); 3.88 (s, 3H); 3.52–3.19 (m, 2H); 2.49 (m, 1H); 1.82–1.47 (m, 8H).

EXAMPLE 30

Synthesis of 1-(3-Cyclopentyloxy-4-methoxy-2-nitro-phenyl)-2-(3,5-dichloro-pyridin-4-yl-methyl)-ethanone A solution of 1-(3-cyclopentyloxy-4-methoxy-2-nitro-phenyl)-2-(3,5-dichloro-pyridin-4-yl-methyl)-ethanol (32 g, 75 mmoles), obtained as described in example 29, in methylene chloride (400 ml) was added with KBr (0.9 g, 7.5 mmoles) in water (90 ml), then with TEMPO® (2,2,6,6-tetramethyl-piperidinyloxy) (3.2 g) and 0.54M NaClO (200 ml, 108.3 mmoles). The temperature was kept under 5° C. during the additions, then at 0° C. for 2 hours with stirring. The mixture was diluted with water, the phases were separated and the organic one washed with an aqueous solution of sodium thiosulfate, discoloured with charcoal, anhydrified and concentrated under vacuum. The residue was tritured with isopropyl ether to give 31 g of the title product (yield: 97%).

$^1$H-NMR (200 MHz, CDCl$_3$) δ (ppm): 8.46 (s, 2H); 7.71 (d, 1H, JHH=8.8 Hz); 7.03 (d, 1H); 5.12–5.04 (m, 1H); 4.55 (m, 2H); 3.96 (s, 3H); 1.86–1.46 (m, 8H).

EXAMPLE 31

Synthesis of 1-(2-Amino-3-cyclopentyloxy-4-methoxy-phenyl)-2-(3,5-dichloro-pyridin-4-yl-methyl)-ethanone A solution of 1-(3-cyclopentyloxy-4-methoxy-2-nitro-phenyl)-2-(3,5-dichloro-pyridin-1-yl-methyl)-ethanone (30.5 g, 72 moles), obtained as described in example 30. and iron dust (24 g, 432 moles) in acetic acid (200 ml) was kept under nitrogen at reflux overnight, then brought to room temperature and dried under vacuum. The residue was taken up in water and brought to pH=7–8 with concentrated NaOH, extracted in ethyl acetate and filtered over celite. The aqueous phase was twice extracted in ethyl acetate. The organic phases were anhydrified and dried under vacuum. The residue was tritured with isopropyl ether to give 26.08 g of the title product (yield: 91%).

$^1$H-NMR (200 MHz, CDCl$_3$) δ (ppm): 8.49 (s, 2H); 7.60 and 6.33 (2d, 2H, JHH=9.2 Hz); 5.77 (m, 2H); 4.89–4.82 (m, 1H); 4.61 (s, 2H); 3.90 (s, 3H); 1.90–1.54 (m, 8H).

EXAMPLE 32

Synthesis of 1-(3-Cyclopentyloxy-2-formamino-4-methoxy-phenyl)-2-(3,5-dichloro-pyridin-4-yl-methyl)-ethanone A solution of 1-(2-amino-3-cyclopentyloxy-4-methoxy-phenyl)-2-(3,5-dichloro-pyridin-4-yl-methyl)-ethanone (1 g, 2.53 moles), obtained as described in example 31, in formic acid (20 ml), under stirring and dry nitrogen at 0° C., was added with acetic anhydride (3.4 ml, 35.4 moles) and the mixture was kept at fixed temperature for 20 minutes then brought to 55° C. After 1.5 hours it was cooled, added with 32% NaOH to pH=8–9, extracted in ethyl acetate, and the organic phases were washed with water, anhydrified and dried to give 1.1 g of the title product (quantitative yield).

$^1$H-NMR (200 MHz, CDCl$_3$) δ (ppm): 9.90 (m, 1H); 8.93 (m, 1H); 8.50 (s, 2H); 7.78 (d, 1H, JHH=8.8 Hz); 4.81–4.75 (m, 1H); 4.62 (s, 2H); 3.97 (s, 3H); 1.86–1.51 (m, 8H).

EXAMPLE 33

Synthesis of 8-Cyclopentyloxy-3-(3,5-dichloro-pyridin-4-yl)-7-methoxy-1H-quinolin-4-one (Compound 7)

A suspension of 1-(3-cyclopentyloxy-2-formamino-4-methoxy-phenyl)-2-(3,5-dichloro-pyridin-4-yl-methyl)-ethanone (1 g, 2.36 mmoles), obtained as described in example 32, in ethanolic ammonia (20 ml) was refluxed under stirring. After 4 hours the temperature was brought to room value for 1 night, and the reaction mixture was concentrated under vacuum to give a residue which was crystallized from isopropanol, filtered and dried to give 0.96 g of the title product (quantitative yield).

$^1$H-NMR (200 MHz, CDCl$_3$) δ (ppm): 8.79 (d broad, 1H); 8.55 (s, 2H); 8.11 and 7.05 (2d, 2H, JHH=9.2 Hz); 7.62 (d, H, JHH=6.2 Hz); 5.23–5.16 (m, li); 3.98 (s, 3H); 1.9–1.63 (m, 8H).

EXAMPLE 34

Synthesis of N-{2-Cyclopentyloxy-6-[(3,5-dichloro-pyridin-4-yl-methyl)acetyl]-3-methoxy-phenyl}-malonaminic Acid Methyl Ester A solution under nitrogen of 1-(2-amino-3-cyclopentyloxy-4-methoxy-phenyl)-2-(3,5-dichloro-pyridin-4-yl-methyl)-etanone (4 g, 10 moles), obtained as described in example 31, in acetic acid (50 ml) was added with methyl-malonyl cliloride (1.32 ml, 11 moles), and the mixture was left under stirring overnight, then dried under vacuum, taken up in methylene chloride, twice washed with an aqueous solution of NaHCO$_3$ and concentrated under vacuum to give a residue which tritured with isopropyl ether gave 3.68 g of the title product (yield: 74%).

$^1$H-NMR (200 MHz, CDCl$_3$) δ (ppm): 9.39 (m, 1H); 8.47 (s, 2H); 7.58 (d, 1H, JHH=8.8 Hz); 6.83 (d, 1H); 4.87–4.79 (m, 1H); 4.60 (s, 2H); 3.90 (s, 3H); 3.73 (s, 3H); 3.40 (s, 2H); 1.86–1.50 (m, 8H).

EXAMPLE 35

Synthesis of 8-Cyclopentyloxy-4-(3,5-dichloro-pyridin-4-yl-methyl)-7-methoxy-2-oxo-1,2-dihydro-quinolin-carboxylic Acid Methyl Ester (Compound 8)

Under nitrogen, using dry methanol (50 ml) and metal sodium (0.16 g, 6.93 moles), sodium methoxide was prepared and added with N-{2-cyclopentyloxy-6-[(3,5-dichloro-pyridin-4-yl-methyl)acetyl]-3-methoxy-phenyl}-malonaminic acid methyl ester (3.14 g, 6.3 moles), obtained as described in example 34. The mixture was stirred at room temperature for 1 hour then treated with 10% HCl and extracted in ethyl acetate, dried under vacuum and taken up in methylene chloride and water. The aqueous phase was twice extracted in methylene chloride. The organic phases were anhydrified and dried under vacuum to give a residue which was crystallized from acetonitrile (30 volumes) to give 1.51 g of the title product (yield: 50%).

$^1$H-NMR (200 MHz, CDCl$_3$) δ (ppm): 9.00 (m, 1H); 8.45 (s, 2H); 7.28–6.80 (2d, 2H, JHH=9.2 Hz); 5.13–5.05 (m, 1H); 4.51 (s, 2H); 3.91 (s, 3H); 3.58 (s, 3H); 1.89–1.56 (m, 8H).

EXAMPLE 36

Synthesis of 8-Cyclopentyloxy-3-(3,5-dichloro-pyridin-4-yl)-7-methoxy-2-methyl-2,3-dihydro-1H-quinolin-4-one (Compound 9)

A solution under nitrogen of 1-(2-amino-3-cyclopentyloxy-4-methoxy-phenyl)-2-(3,5-dichloro-pyridin-4-yl-methyl)-ethanone (1.5 g, 3.8 moles), obtained as described in example 31, in acetic acid (25 ml), was added with acetaldehyde and the mixture was heated to 80° C. then left to stand overnight, concentrated under vacuum, taken up in methylene chloride and washed with an aqueous solution of NaHCO$_3$. The organic phase was discoloured with charcoal, filtered over celite and concentrated under vacuum to give a residue which was purified by flash chromatography (eluent: petrolatum 40:60°/acetone 8:2, then 85:15). The eluate was dissolved in isopropyl ether (4 ml) to give a precipitate which filtered, washed with isopropyl ether, dried under vacuum at 40° C. gave 1.1 g of the title product (yield: 69%).

$^1$H-NMR (200 MHz, CDCl$_3$) δ (ppm): 8.53–8.45 (s broad, 2H); 7.66 (d, 1H, JHH=9 Hz); 6.43 (d, 1H); 4.93–4.85 (m, 1H); 4.82 (s, 1H); 4.53–4.30 (m, 2H); 3.89 (s, 3H); 1.92–1.61 (m, 8H); 1.17 (d, 1H, JHH=5.9 Hz).

EXAMPLE 37

Synthesis of 1-(3-Cyclopentyloxy-4-methoxy-6-nitro-phenyl)-2-(3,5-dichloro-pyridin-4-yl-methyl)-ethanol Operating analogously to example 29 using 2M lithium diisopropylamide in tetrahydrofuran/heptane/ethylbenzene (35 ml, 69.3 mmoles) in dry tetrahydrofuran (70 ml), 3,5-dichloro-4-methyl-pyridine (10.7 g, 66 mmoles), obtained as described in example 15, in dry tetrahydrofuran (70 ml), and 3-cyclopentyloxy-4-methoxy-6-nitro-benzaldehyde (17.5 g, 66 mmoles) obtained as described in example 28, in dry tetrahydrofuran (70 ml), 24.52 g of the title product were obtained (yield: 87%).

$^1$H-NMR (200 MHz, CDCl$_3$) δ (ppm): 8.37 (s, 2H); 7.52 (s, 1H); 7.15 (s, 1H); 5.83–5.76 (m, 1H); 5.83–5.76 (m, 2H); 4.86–4.78 (m, 1H); 3.88 (s, 3H); 3.48–3.44 (m, 2H); 2.70 (m, 1H); 2.03–1.55 (m, 8H).

EXAMPLE 38

Synthesis of 1-(3-Cyclopentyloxy-4-methoxy-6-nitro-phenyl)-2-(3,5-dichloro-pyridin-4-yl-methyl)-ethanone Operating analogously to example 30 using 1-(3-cyclopentyloxy-4-methoxy-6-nitro-phenyl)-2-(3,5-dichloro-pyridin-4-yl-methyl)-ethanol (28 g, 66 mmoles), obtained as described in example 37, in methylene chloride (500 ml), KBr (0.785 g, 6.6 mmoles) in water (80 ml), TEMPO® (2.8 g) and 0.54M NaClO (160 ml, 85.8 mmoles) 28.55 g of the title product were obtained (yield: 97%).

$^1$H-NMR (200 MHz, CDCl$_3$) δ (ppm): 8.50 (s, 2H); 7.63 (s, 1H); 6.72 (s, 1H); 4.84–4.76 (m, 1H); 4.51 (s, 2H); 3.93 (s, 3H); 2.04–1.55 (m, 8H).

EXAMPLE 39

Synthesis of 1-(6-Amino-3-cyclopentyloxy-4-methoxy-phenyl)-2-(3,5-dichloro-pyridin-4-yl-methyl)-ethanone Operating analogously to example 31 using 1-(3-cyclopentyloxy-4-methoxy-6-nitro-phenyl)- 2-(3,5-dichloro-pyridin-4-yl-methyl)-ethanone (26.75 g, 63 moles), obtained as described in example 38, and iron dust (21.1 g, 378 moles) in acetic acid (120 ml) 18.7 g of the title product were obtained (yield: 75%).

$^1$H-NMR (200 MHz, CDCl$_3$) δ (ppm): 8.49 (s, 2H); 7.28 (s, 1H); 6.15 (s, 1H); 5.75 (m, 2H); 4.73–4.64 (m, 1H); 4.55 (s, 2H); 3.85 (s, 3H); 1.93–1.54 (m, 8H).

EXAMPLE 40

Synthesis of 6-Cyclopentyloxy-3-(3,5-dichloro-pyridin-4-yl)-7-methoxy-1H-quinolin-4-one (Compound 10)

A solution of 1-(6-amino-3-cyclopentyloxy-4-methoxy-phenyl)-2-(3,5-dichloro-pyridin-4-yl-methyl)-ethanone (2 g, 5.06 mmoles), obtained as described in example 39, in glacial acetic acid (50 ml) was added under stirring and dry nitrogen with triethylorthoformate (1.7 ml, 10.1 mmoles), then heated to 100° C. After 30 minutes the mixture was cooled in water/ice, added with NaOH to pH=6 and extracted in ethyl acetate. The organic phase was washed with water, anhydrified and concentrated. The residue was chromatographed (flash) over silica gel (eluent: methylene chloride/methanol 95:5) to give a solid which was crystallized from ethyl acetate (230 ml) in water bath to give 0.85 g of the title product (yield: 42%).

$^1$H-NMR (200 MHz, CDCl$_3$) δ (ppm): 12.56 (d. 1H, JHH=6.4 Hz); 8.18 (s, 2H). 7.64 and 6.85 (2s, 2H); 7.49 (d, 1H); 4.77–4.69 (m, 1H); 3.82 (s, 3H); 1.88–1.42 (m, 8H).

EXAMPLE 41

Synthesis of N-{4-Cyclopentyloxy-2-[(3,5-dichloro-piridin-4-yl-methyl)acetyl]-5-methoxy-phenyl}-malonaminic Acid Methyl Ester Operating analogously to example 34 using 1-(6-amino-3-cyclopentyloxy-4-methoxy-phenyl)-2-(3,5-dichloro-pyridin-4-yl-methyl)-ethanone (2 g, 5 moles), obtained as described in example 39, in acetic acid (25 ml) and methylmalonyl chloride (0.65 ml, 6 moles), 2.3 g of the title product were obtained (yield: 93%).

$^1$H-NMR (200 MHz, CDCl$_3$) δ (ppm): 11.80 (m, 1H); 8.51 (s, 2H); 8.48 and 7.44 (s, 2H); 4.84–4.76 (m, 1H); 4.62 (s, 2H); 3.93 (s, 3H); 3.72 (s, 3H); 3.44 (s, 2H); 1.96–1.55 (m, 8H).

EXAMPLE 42

Synthesis of 6-Cyclopentyloxy-4-(3,5-dichloro-piridin-4-ylmethyl)-7-methoxy-2-oxo- 1,2-dihydro-quinolin-3-carboxylic Acid Methyl Ester (Compound 11)

Operating analogously to example 35 using dry methanol (100 ml), metallic Na (0.25 g, 4.6 mmoles), N-{4-cyclopentyloxy-2-[(3,5-dichloro-pyridin-4-ylmethyl)acetyl]-5-methoxy-phenyl}-malonaminic acid methyl ester (2.3 g, 4.6 moles), obtained as described in example 41, 0.95 g of the title product was obtained (yield: 43%).

$^1$H-NMR (200 MHz, CDCl$_3$) δ (ppm): 12.43 (m, 1H); 8.45 (s, 2H); 6.80 (s. 2H); 4.55 (s, 2H); 4.57–4.49 (m, 1H); 3.90 (s, 3H); 3.72 (s, 3H); 1.77–1.55 (m, 8H).

EXAMPLE 43

Synthesis of 6-Cyclopentyloxy-3-(3,5-dichloro-pyridin-4-yl)-7-methoxy-2,3-dihydro-1H-quinolin-4-one (Compound 12)

Operating analogously to example 36 using 1-(6-amino-3-cyclopentyloxy-4-methoxy-phenyl)-2-(3,5-dichloro-pyridin-4-yl-methyl)-ethanone (2 g, 5 moles), obtained as described in example 39, in acetic acid (50 ml), and paraformaldehyde (0.16 g, 5.25 moles) 0.821 g of the title product was obtained (yield: 62%).

$^1$H-NMR (200 MHz, CDCl$_3$) δ (ppm): 8.47 (s broad, 2H); 7.35 and 6.11 (2s, 2H); 4.80–4.66 (m, 2H); 4.38 (m, 1H); 4.19–3.37 (m, 2H); 3.83 (s, 3H); 1.97–1.48 (m, 8H).

EXAMPLE 44

Synthesis of 6-Cyclopentyloxy-3-(3,5-dichloro-pyridin-4-yl)-7-methoxy-1-methyl-2,3-dihydro-1H-guinolin-4-one (Compound 13)

A solution under nitrogen of 6-cyclopentyloxy-3-(3,5-dichloro-pyridin-4-yl)-7-methoxy-2,3-dihydro-1H-quinolin-4-one (0.36 g, 0.88 mmoles), obtained as described in example 43, in formic acid (10 ml) was added with paraformaldehyde (0.098 g, 3.6 mmoles). The mixture was heated to 50° C. for 1 hour, left to stand overnight, dried under vacuum taken up in ethyl acetate, washed with an aqueous solution of Na$_2$CO$_3$, anhydrified and dried under vacuum. The residue was purified by silica gel flash chromatography (eluent: petrolatum 60:80/ethyl acetate 8:2) to give a residue which was tritured in isopropyl ether to give 0.2 g of the title product (yield: 62%).

$^1$H-NMR (200 MHz, CDCl$_3$) δ (ppm): 8.48 (s, 2H); 7.46 and 6.17 (2s, 2H) 4.89–4.79 (m, 1H); 4.78–4.70 (m, 1H); AB part of ABX system: V$_a$=4.08, V$_b$=3.27, J$_{ab}$=12.9 Hz, J$_{ax}$=11.3 Hz, J$_{bx}$=6.1 Hz); 3.92 (s, 3H); 3.00 (s, 3H); 1.95–1.51 (m, 8H).

EXAMPLE 45

Sinthesis of N-[2-(2-cyclopentyloxy-3-methoxy-phenyl)-ethyl]-2-pyridin-4-yl-acetamide A suspension under nitrogen of 4-pyridin-acetic acid (0.43 g, 2.48 mmoles) hydrochloride in dioxane (20 ml) was added with triethylamine (0.34 ml, 0.25 g, 2.48 mmoles) and heated in water-bath to 40° C. for 10 minutes, then cooled and added with HOBT (0.33 g, 2.48 mmoles) and DCC (0.51 g, 2.48 mmoles). After 45 minutes a solution of 2-(2-cyclopentyloxy-3-methoxy-phenyl)-ethylanine (0.53 g, 2.25 mmoles), obtained as described in example 3 then desalted, in dioxane (5 ml) was dropped therein. After 1 hour the formed solid was filtered and washed with dioxane, then dried, taken up in ethyl acetate, filtered and washed with aqueous $NaHCO_3$, then with water. The mother liquor was anhydrified and dried to give an oil which was purified by flash chromatography (eluent: methylene chloride/methanol 99:1 to 93:7) to give 0.57 g of the title product (yield: 71%).

EXAMPLE 46

Synthesis of 5-Cyclopentyloxy-6-methoxy-1-pyridin-4-ylmethyl-3,4-dihydro-isoquinoline (Compound 14)

A solution of N-[2-(2-cyclopentyloxy-3-methoxy-phenyl)-ethyl]-2-pyridin-4-yl-acetamide (0.52 g, 1.47 mmoles), obtained as described in example 45, in toluene (5 ml) was added with phosphoryl chloride (0.40 ml, 0.67 g, 4.4 mmoles) and heated to 80° C. After 1 hour the mixture was cooled, diluted with methylene chloride, extracted with 1N NaOH (15+5 ml) keeping the pH at basic value. The organic phase was separated, concentrated, taken up in methylene chloride and washed with water, then anhydrified and dried to give an oil which was purified by flash chromatography (eluent: methylene chloride/methanol 97.5:2.5 then 95:5) to give 0.038 g of the title product.

$^1$H-NMR (200 MHz, $CDCl_3$) δ (ppm): 8.45–7.15 (m, 4H); 7.07 and 7.65 (2d, JHH=8.6 Hz); 4.69 (m, 1H); 3.98 (s, 2H); 3.79 (s, 3H); 3.67–3.60 (m, 2H); 2.72–2.65 (m, 2H); 1.85–1.51 (m, 8H).

EXAMPLE 47

Synthesis of N-[2-(2-cyclopentyloxy-3-methoxy-phenyl)-ethyl]-2-pyridin-3-yl-acetamide A suspension of 2-(2-cyclopentyloxy-3-methoxy-phenyl)-ethylamine hydrochloride (0.5 g, 1.84 mmoles), obtained as described in example 3, in methylene chloride (10 ml) was added with trethylanmine (0.84 ml, 0.61 g, 6.07 mmoles) then, portionwise, with nicotinic acid hydrochloride (0.36 g, 2.02 mmoles) while keeping the pH at basic value. The mixture was poured into water and the organic phase was washed with water, anhydrified and dried to give an oil which was purified by flash chromatography (eluent: ethyl acetatelpetrolatum 7:3) yielding 0.57 g of the title product (yield: 90%).

EXAMPLE 48

Synthesis of 5-Cyclopentyloxy-6-methoxy-1-pyridin-3-ylmethyl-3,4-dihydro-isoquinoline Dihydrochloride (Compound 15)

N-[2-(2-cyclopentyloxy-3-methoxy-phenyl)-ethyl]-2-pyridin-3-yl-acetamide (0.174 g, 0.51 mmoles), obtained as described in example 47, and phosphoryl chloride (0.47 ml, 5.11 mmoles) were heated to 70° C. under nitrogen. The mixture was washed and dried and the residue taken up in acetonitrile, then poured into a solution of NaOH. The organic phase was washed with an aqueous saturated solution of NaCl, anhydrified and concentrated to give an oil which was purified by flash chromatography (cluent: methylene chloride/methanol 97:3 then 95:5). The eluate was dissolved in ethyl ether and acidified with etheral HCl to give a precipitate of 0.179 g of the title product (yield: 56%).

$^1$H-NMR (200 MHz, DMSO) δ (ppm): 13.41 (s broad, H+); 8.96–7.72 (m, 4H); 7.23–7.14 (m, 2H); 4.90–4.82 (m, 1H); 3.95 (s, 3H); 3.94–3.87 (m, 2H); 3.17–3.09 (m, 2H); 1.82–1.57 (m, 8H).

EXAMPLE 49

Synthesis of 3-(5-Cyclopentyloxy-6-methoxy-2-oxy-3,4-dihydro-isoquinolin-1-ylmethyl)-pyridine 1-oxide (Compound 16)

A solution of 5-cyclopentyloxy-6-methoxy-1-pyridin-3-yl-methyl-3,4-dihydro-isoquinoline dihydrochloride (0.69 g, 2.14 mmoles), obtained as described in example 48, in methylene chloride (10 ml) was added with 70% m-chloroperbenzoic acid (1.06 g, 4.28 mmoles). After 1.5 hours further 70% m-chloroperbenzoic acid (0.53 g, 2.14 mmoles) and methyiene chloride (5 ml) were added. After 40 minutes the mixture was poured into 5% $NaHCO_3$ and the organic phase was anhydrified and concentrated to give a crude which was purified by flash chromatography (eluent: methylene chloride/methanol 96:4 to 92:8). The eluate was tritured in ethyl ether to give 0.308 g of the title product.

$^1$H-NMR (200 MHz, $CDCl_3$) 5 (ppm): 8.40–7.32 (m, 4H); 6.71 and 6.58 (2d, 2H, JHH=8.6 Hz); 4.91 4.83 (m, 1H); 4.204. 13 (m, 2H); 3.85 (s, 3H); 3.25–3.17 (m, 2H); 1.89–1.57 (m, 8H).

EXAMPLE 50

Synthesis of N-[2-(2-Cyclopentyloxy-3-methoxy-phenyl)-ethyl]-2-pyridin-4-yl-acetamide Operating analogously to example 46 using 2-(2-cyclopentyloxy-3-methoxy-phenyl)-ethylamine hydrochloride (1 g, 3.68 mmoles), obtained as described in example 3, in methliene chloride (20 ml), triethylamine (1.69 ml, 1.23 g, 12.14 mmoles) and isonicotinic acid hydrochloride (0.72 g, 4.05 mmoles), 1.42 g of the title product were obtained (yield: 99.9%).

EXAMPLE 51

Synthesis of 5-Cyclopentyloxy-6-methoxy-1-pyridin-4-yl-3,4-dihydro-isoquinoline (Compound 17)

Operating analogously to example 48 using N-[2-(2-cyclopentyloxy-3-methoxy-phenyl)-ethyl]-2-pyridin-4-yl-acetamide (1.24 g, 3.65 mmoles), obtained as described in example 50, and phosphoryl chloride (3.35 ml, 36.5 mmoles) 0.59 g of the title product was obtained (yield: 50%).

$^1$H-NMR (200 MHz, DMSO) δ (ppm): 8.96–8.92 (m, 2H); 7.79–7.75 (m, 2H); 7.14 (s, 2H); 4.89–4.83 (m, 1H); 3.94 (s, 3H); 3.96–3.88 (m, 2H); 3.17–3.09 (m, 2H); 1.84–1.55 (m, 8H).

EXAMPLE 52

Synthesis of 5-Cyclopentyloxy-6-methoxy-1-(1-oxy-pyridin-4-yl)-3,4-dihydro-isoquinoline 2-Oxide (Compound 18)

Operating analogously to example 49 using 5-cyclopentyioxy-6-methoxy-l-pyridin-4-yl-3,4-dihydroisoquinoline (0.59 g, 1.83 mmoles), obtained as described in example 51, in methylene chloride (10 ml), and 70% m-chloroperbenzoic acid (0.45 g, 1.83 mmoles), 0.231 g of the title product was obtained.

$^1$H-NMR (200 MHz, CDCl$_3$) δ (ppm): 8.25–7.64 (m, 4H); 6.74 and 6.64 (2d, 2H, JHH=8.6 Hz); 4.90–4.83 (m, 1H); 4.18–4.11 (m, 2H); 3.86 (s, 3H); 3.22–3.15 (m, 2H); 1.89–1.58 (m, 8H).

EXAMPLE 53

PDE 4 Enzyme Inhibition Study a) Purification of Human Polymorphonucleate Leukocytes The polymorphonucleate leukocytes (PMNs) were isolated from peripheral blood of healthy volunteers according to what described by Boyum A., Scand. J. Immunol., 1976, 50 suppl., 9). Shortly, the isolation of the PMNs was effected by Ficoll-Paque gradient centrifugation followed by sedimentation on dextrane and the erythrocyte contanunation was eliminated by hypotonic lysis.

b) PDE 4 Enzyme Purification

The human PMNs were re-suspended in TRIS/HCl buffer (10 mM pH 7.8) containing MgCl$_2$ (5 mM), EGTA (4 mM), mercaptoethanol (5 mM), TRITON-X100 (1%), pepstatin A (1 μM), PMSF (100 μM) and leupeptin (1 μM), and homogenized by Polytron. The homogenate was centrifuged at 25,000×g per 30 minutes at 4° C. and the sumatant was used for the PDE 4 enzyme purification by ion exchange chromatography using the FPLC technique according to what described by Schudt C. et al., Naunyn-Schmidberg's Arch. Pharmacol., 1991, 334, 682. The surnatant was seeded on a UNO Q12 column (Bio-Rad) and the enzyme was eluted by sodium acetate gradient from 50 mM to 1M. The fractions containing enzymatic activity were joined, dialysed against water and concentrated. The resulting PDE 4 enzyme was stored at −20° C. in the presence of ethylenglycole (30%) v/v) till the use c) PDE 4 Enzyme Inhibition The enzyme activity was evaluated with an Amersham kit based on the SPA technique (Scintillation Proximity Assay). The enzymatic reaction was effected in a total volume of 100 μl of TRIS/HCl buffer (50 mM, pH7.5), MgCl$_2$, (8.3 mM), EGTA (1.7 mM), cAMP (1 μM) and [$^3$H]cAMP (~100.000 dpm). The compounds of the invention were added at the wanted concentrations. The reaction was started by adding the enzyme (15 μg protein/ml) in 40 minutes at 30° C. and stopped by adding 50 μl of suspension of SPA particles. The radioactivity due to the particles was measured in β-emitting counter. The IC$_{50}$ values were calculated on 9 equidistant concentrations in logarithmic scale using a 4-parameters logistic function by a software. The results are set forth in Table 1.

TABLE 1

| Compound | PDE 4% inibition | | IC$_{50}$ nM |
| --- | --- | --- | --- |
| | 10$^{-5}$M | 10$^{-6}$M | |
| 1 | 96 | 79 | 148 ± 18 |
| 2 | 88 | 54 | 1050 ± 191 |
| 3 | | 93 | 87.5 ± 17 |
| 4 | | 54 | |
| 8 | | 60 | |
| 10 | | 73 | |
| 12 | 100 | 94 | 101 ± 21 |

EXAMPLE 54

TNF$_α$ Inhibition Test a) Human Monocytes Isolation

The monocytes were isolated from peripheral blood of healthy volunteers according the procedure of Schreek L., J. Natl. Cancer Inst., 1964, 32, 507. The monocytes and lymphocytes population was isolated by Ficoll gradient centrifugation, and the cells diluted at a density of 2.5×10$^6$ cells/ml in RPMI1640 incubation containing 1% inactivated bovine fetal serum, penicillin (100 U/ml) and streptomycin (100 U/ml) were placed in 24-wells plates (1 ml/well) and left to adhere for 1 hour at 37° C. with 5% CO$_2$. At the end of the incubation the lymphocytes not adhering were removed by aspiration and the monocytes adhered to the plate were used in the next step.

b) TNF$_α$ Synthesis Inhibition

The TNF$_α$ synthesis from human monocytes was measured according to the method of Barnette M. et al., Biochemical Pharmacology, 1996, 51, 949. The monocytes were incubated for 1 hour with 1 ml of RPMI1640 incubation medium (1% inactivated bovine serum, 100 U/ml penicillin and streptomycin) containing different concentrations of the products according to the present invention or the carrier only for the controls. The TNF$_α$ synthesis from monocytes was induced by adding 1 ng/ml of LPS (lipopolysaccharide of E. Coli) and after 16 hours of incubation at 37° C., 5% CO$_2$, the incubation medium was removed, and the surnatant stored at −80° C. until the measurement. The TNF$_α$ levels were determined by ELISA test with an Amersham kit. The results are set forth in Table 2 as IC$_{50}$ measured with the same calculation of example 53.

TABLE 2

| Compound | IC$_{50}$ nM |
| --- | --- |
| 1 | 252 ± 67 |
| 3 | 83 ± 16 |
| 12 | 78.7 ± 16 |

EXAMPLE 55

PDE 3 and 5 Enzymes Inhibition Test a) Human Platelet Preparation

Human platelets were prepared from platelet rich plasma (PRP) obtained from the Hematological Dept. of the "L. Sacco" Hospital of Milan. The PRP was centrifuged at 2,200 rpm for 15 minutes at 4° C. and the pellet was suspended in lysis solution (15 ml; 155 mM NH$_4$Cl, 10 mM KHCO$_3$ and 0.1 mM Na$_2$EDTA, pH=7.4) and incubated for 10 minutes on ice-bath to remove erythrocyte contamination. After centrifuging at 1,400 rpm for 10 minutes at 4° C., platelets were suspended in 10 ml of 145nM NaCl, 5 mM KCl, 1 mM MgSO$_4$, 10 mM glucose, 10 mM HEPES and 0.05 U/ml of hirudin (pH=7.4), and stored at −20° C. until homogenization and chromatography.

b) Purification of PDE 3 and PDE 5 with Fast Protein Liquid Chromatography (FPLC)

Before the chromatographic step, platelets were thawed and 50 ml of 20 mM TRIS (pH=6.5) containing 5 mM β-mercapto-ethanol, 2 mM EDTA, 50 mM sodium acetate and 50 μM PMSF (homogenization buffer) were added. The platelet suspension was then homogenized by a Polytron homogenizer (Polytron PT 1200) for 20 seconds. The homogenate was centrifuged at 14,500 rpm for 20 minutes at 4° C., and the supernatant was applied to a UNO Q12 column (Bio-Rad) pre-equilibrated with the PMSF. A flow rate of 4.5 ml/min was used throughout the ion exchange chromatography procedure. The column was washed with PMSF (180 ml) and PDE 3 and PDE 5 were eluted by sodium acetate linear gradient from 0.05M to 1M. The fractions containing enzymatic activity were joined, dialyzed against water and concentrated 10 times by ultrafiltration. The resulting solution was stored at −20° C. in the presence of ethylenglycole (30%) v/v) until use.

c) Assay of Phoshodiesterase Activity

The enzyme activity was assessed with an Amersham kit based on the SPA technique (Scintillation Proximity Assay). The enzymatic reaction was effected in a total volume of 100 μl of TRIS/HCl buffer (50 mM, pH7.5), MgCl$_2$ (8.3 mM), EGTA (1.7 mM), cAMP (for PDE 3 assay) or cGMP (for PDE 5 assay) (1 μM), [$^3$H]cAMP or [$^3$H]cGMP (10 μl), and 10 μl of the compounds of the invention. The reaction was started by adding the enzyme (10 μl) incubated for 40 minutes at 30° C. and stopped by adding 50 μl of SPA beads. The radioactivity due to the particles was measured in β-emitting counter. The results are expressed as percent activity versus the control present in each test.

TABLE 3

| Compound | PDE 3 % inhibition (μM) | PDE 5 % inhibition (μM) |
|---|---|---|
| 1 | 0 | 10 |
| 3 | 24 | 12 |
| 12 | 12 | 10 |

What is claimed is:

1. A compound of formula I

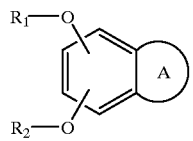

(I)

wherein A is

wherein
  A is substituted by a —B—Cy group wherein B is methylene, ethylene, amino, CONH or a bond and Cy is a 5- or 6-membered heterocycle containing from 1 to 3 nitrogen atom(s) optionally substituted by one or more halogen(s), and A is optionally substituted by (C$_{1-4}$)alkyl, (C$_{1-4}$)alkoxy or COOR', wherein R' is hydrogen or a (C$_{1-4}$)alkyl group
  R$_1$ is a (C1-6)alkyl or polyfluoro(C1-6)alkyl group;
  R$_2$ is aryl, aryl-(C1-10)-alkyl or a (C4-7)cycloalkyl group optionally containing an oxygen atom and optionally substituted by a polar substituent;
  and the N→O derivatives and pharmaceutically acceptable salts thereof.

2. A compound according to claim 1 wherein Cy is a 6-membered heterocycle containing from 1 to 3 nitrogen atom(s) substituted by one or more halogen(s) and the pharmaceutically acceptable salts thereof.

3. A compound according to claim 1 wherein A is

optionally substituted by (C1-4)alkyl or —COOR'—, B is methlene and cy is a 6-membered heterocycle containing from 1 to 3 nitrogen atom(s) substituted by one or more halogen(s) and the pharmaceutically acceptable salts thereof.

4. A compound containing a therapeutically effective amount of a compound according to claim 1 in admixture with a suitable carrier.

5. A compound according to claim 4 for treating allergic and inflammatory pathologies.

6. A compound according to claim 4 for treating respiratory diseases.

* * * * *